United States Patent [19]

Alvarez et al.

[11] Patent Number: 4,710,624
[45] Date of Patent: Dec. 1, 1987

[54] APPARATUS AND METHOD FOR MEASURING LIGHT TRANSMITTANCE OR REFLECTANCE

[75] Inventors: Robert Alvarez, Mountain View; Leonard Lehmann, Redwood City; Bruno Strul, Palo Alto, all of Calif.

[73] Assignee: DigiRad Corporation, Palo Alto, Calif.

[21] Appl. No.: 608,747

[22] Filed: May 10, 1984

[51] Int. Cl.[4] ............................................. G02B 26/10
[52] U.S. Cl. .................................... 250/228; 250/235; 358/293
[58] Field of Search ........................ 250/228, 234–236; 358/285, 293, 294, 296, 302

[56] References Cited

U.S. PATENT DOCUMENTS

| | | | |
|---|---|---|---|
| 4,314,283 | 2/1982 | Kramer | 250/228 |
| 4,370,678 | 1/1983 | Kitamura | 358/294 |
| 4,453,180 | 6/1984 | Juergensen | 250/228 |

*Primary Examiner*—Edward P. Westin
*Attorney, Agent, or Firm*—Townsend and Townsend

[57] ABSTRACT

Apparatus and a method for providing measurements of the diffuse transmittance or reflectance of a sheet at a set of points arranged along a pattern line on the sheet. In accordance with the invention, the sheet, such as a photographic film, is moved with respect to a cylinder with a slot cut in its wall parallel to its central axis. A beam of radiation is swept parallel to the slot and into the cylinder after scanning along a line on the sheet. The inner wall surface of the cylinder is coated with a high reflectance material so that a fraction of the directly transmitted and scattered radiation in the cylinder enters one or more electronic radiation detectors coupled to the cylinder. The fraction of the radiation measured depends on the position along the slot of the radiation beam, and the data are corrected by dividing the measurement at each point by the measured radiation at that point when no object is in the beam. Several embodiments of the cylinder are disclosed.

20 Claims, 7 Drawing Figures

APPARATUS AND METHOD FOR MEASURING LIGHT TRANSMITTANCE OR REFLECTANCE

BACKGROUND OF THE INVENTION

1. Field of the Invention

This invention relates to systems for measuring the transmittance or reflectance of thin sheets, such as photographic films or other transparencies, having images and other information thereon. In a primary application, the invention relates to scanning systems where the transmittance or reflectance of a whole sheet is measured by scanning a spot of light throughout the sheet and measuring the amount of light transmitted or reflected at each point of the scan.

2. Description of the Prior Art

The light transmittance of a sheet is defined as the ratio of the intensity of light passing through a point on the sheet to the light incident on that point. Similarly, the reflectance of the sheet is defined as the ratio of the intensity of light reflected from a point to the intensity of light incident on that point.

It is often desirable to measure the transmittance or reflectance at an array of points along the sheet. Scanners, i.e., machines for automatically making these measurements, have been known and used in the past. They have wide application in the processing of images in medical analyses, graphic arts, and long distance communications.

A major problem in measuring transmittance of a sheet is collecting the light transmitted through the sheet. Several things can happen to light when it interacts with the material in the sheet. One is that the light can pass through the sheet without interacting at all. Another is that the light can be scattered or changed in direction, but still pass through the sheet. Still another possibility is that the light can be absorbed and transfer its energy to the material.

In measuring transmittance, if only the light that passes through the sheet without interacting is used, the resulting ratio of transmitted to incident light is called the specular transmittance. If all the light, including the scattered light, is measured, the resulting ratio is called the diffuse transmittance. There are analogous definitions for light specularly reflected from an opaque sheet (specular reflectance) and light directly reflected and scattered from a sheet (diffuse reflectance).

For practical considerations, it is highly desirable for a scanner to measure diffuse transmittance or reflectance rather than specular transmittance or reflectance. Although the specular and diffuse measurements are related, the specular transmittance or reflectance changes a great deal more for a particular sheet than the diffuse transmittance or reflectance. The ratio of the logarithm of diffuse to the logarithm of specular transmittance, called the Callier coefficient, can be as high as 1.5. This means that if the diffuse transmittance is 0.01 the specular transmittance will be 0.001. The much smaller amount of light collected by a specular measurement can lead to substantial difficulties in design of light measurement electronics.

Previous transmittance and reflectance measurement scanners placed the light collection optics close to the film to collect as much of the scattered light as possible. These scanners then moved the light collection optics and light source with respect to the film, as on a drum scanner where the film is wrapped around a drum and then the drum is rotated. The light source and light collection optics are then scanned longitudinally to measure the transmittance throughout the film. While this technique is widely used, it is a slow one since it involves mechanical motion in both directions, and wrapping the film around the drum makes automatic film handling difficult.

The light collection optics of some systems that measure diffuse transmittance use an integrating sphere. This sphere has a small hole through which light enters and further has a light detector placed in the wall away from the direct path of the light. The sphere wall is coated with a very high reflectance material so that substantially all the light incident on the wall is reflected. Thus, regardless of the direction of the light entering the sphere, a fixed fraction of the entering light strikes the detector and is measured. To measure the transmittance with an integrating sphere at many points throughout a sheet, the sphere is physically moved across the surface or the sheet is moved with respect to the sphere.

Because of the drawbacks associated with light-collecting systems used with scanners of the type described, a need exists for improvements in such a system. The present invention satisfies this need.

SUMMARY OF THE INVENTION

This invention comprises apparatus and a method for providing measurements of the diffuse transmittance or reflectance of a sheet at a set of points arranged along a longitudinal line on the sheet. A primary object of the invention is to provide an improved light collection system constructed and operated in a manner such that only a single dimensional motion of the film or light source is required to make a two-dimensional set of transmittance or reflectance measurements.

Briefly, in accordance with the invention, a sheet, such as a photographic film, is translated orthogonally with respect to a cylinder with a slot cut in its wall parallel to its central axis. A beam of light focused to a small point is swept parallel to the slot and into the cylinder. The inner wall surface of the cylinder is coated with a high reflectance material so that a fraction of the directly transmitted and scattered light in the cylinder enters one or more electronic light detectors arranged in the wall of the cylinder. The fraction of the light measured depends on the position along the slot of the light beam, so that the data must be corrected later by dividing the measurement at each point by the measured light at that point with no object in the beam.

In another embodiment of the invention, the cylinder is solid and composed of high transmittance material with a high reflectivity coating except along a light entrance slot parallel to the central axis of the cylinder.

In still another embodiment of the invention, a light-diffusing member is placed within the cylinder to decrease the rate of variation of the measured light to make the data correction more accurate and easier to implement.

In a further embodiment, the transmittance or reflectance at several different wavelengths of light is simultaneously measured by using a light source with several different wavelengths and then placing several detectors with filters that pass only a narrow band of wavelengths in front of the detectors. There would be an individual correction curve for each detector. In still a further embodiment, the transmittance or reflectance is measured at many different wavelengths by sequentially measuring it across the whole sheet with light sources producing narrow band light centered at different light wavelengths.

Other objects of this invention will become apparent as the following specification progresses, reference being had to the accompanying drawings for illustrations of several embodiments of the invention.

IN THE DRAWING

Figure 1:
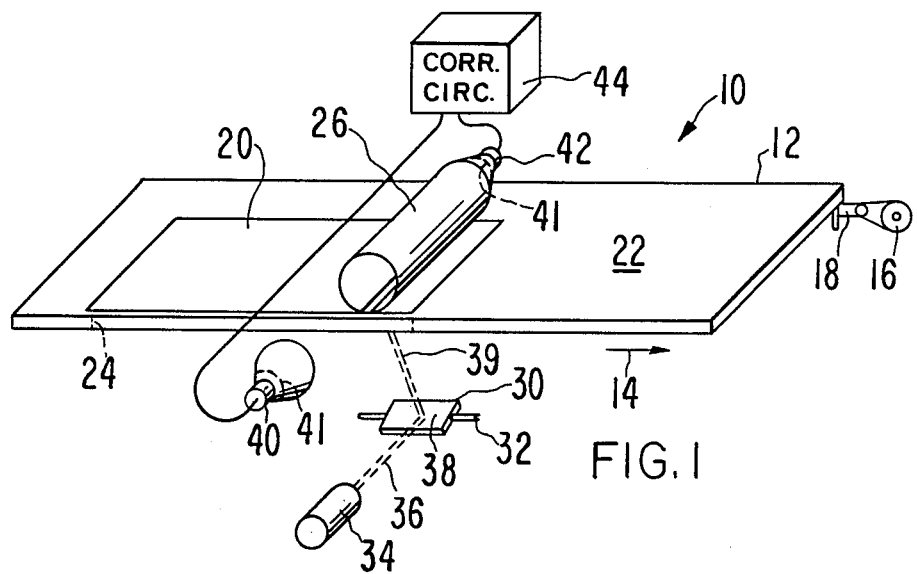
FIG. 1 is a schematic view of a first embodiment of the apparatus of the present invention, the apparatus being arranged to collect light passing through a movable sheet, such as a photographic film.

A first embodiment of the apparatus of the present invention is broadly denoted by the numeral 10 and is shown in FIG. 1 as comprising a base plate or frame 12 which is continously movable in the direction of arrow 14 under the influence of a drive motor 16 coupled by a rotatable lead screw 18 to frame 12. The rotation of the lead screw causes translation of the frame. A sheet 20, such as a photographic film, is placed on the upper surface 22 of frame 12 and is in overlying relationship to an opening 24 through frame 12.

A slotted cylinder 26 is positioned above the frame in any suitable manner in a fixed location above frame 12 and is provided with a slot 28 in the sidewall thereof for receiving light transmitted through sheet 20 after the light has been reflected from a plane mirror 30. The mirror is pivotally mounted below the frame in any suitable manner for rotation about an axis 32 which is generally parallel with the direction of movement of frame 12. A light source 34 directs a beam 36 of light onto a flat face 38 of mirror 30, and the mirror reflects the beam 39 toward and through sheet 20 and into cylinder 26 through slot 28. Since the mirror is rotated about axis 32, the light is swept along a straight line as the frame moves sheet 20 in the direction of arrow 14.

Cylinder 26 has an internal wall surface coated with a highly light-reflecting paint, such as Eastman 6080. A pair of light sensitive detectors 40 and 42 are placed at respective ends of the cylinder. Detectors 40 and 42 typically may be silicon photodiode detectors. They measure the amount of light transmitted through the sheet 20 and into the cylinder and then reflected from the internal wall surface of the cylinder.

The signals from the detectors 40 and 42 are summed to provide a combined signal with less variation as the light beam is swept across slot 28. As the light beam is swept along this slot, the combined signals are digitized by an analog-to-digital converter and then corrected for the variation of the response along the slot by an electronic circuit 44 shown in more detail in FIG. 2a. The correction is the same for the scan along each line measured by cylinder 26. Circuit 44 (FIG. 2a) includes an input latch 46 which receives the sum of the signals from photodetectors 40 and 42. The output of latch 46 is coupled to the input of an adder 48 which is coupled to the output of a memory 45 such as a PROM in which is stored the data received by sensing the light transmittance along a scan line with no sheet 20 on frame 12. The output of adder 48 is coupled to a second latch 50 whose output can then be directed to a computer or other data handling device. An address generator-counter 52 is provided for memory 45. A clock signal on line 54 clocks latches 46 and 50 and counter 52 to read data into and out of adder 48. A reset signal can be provided on line 56 for counter 52.

Figure 2:
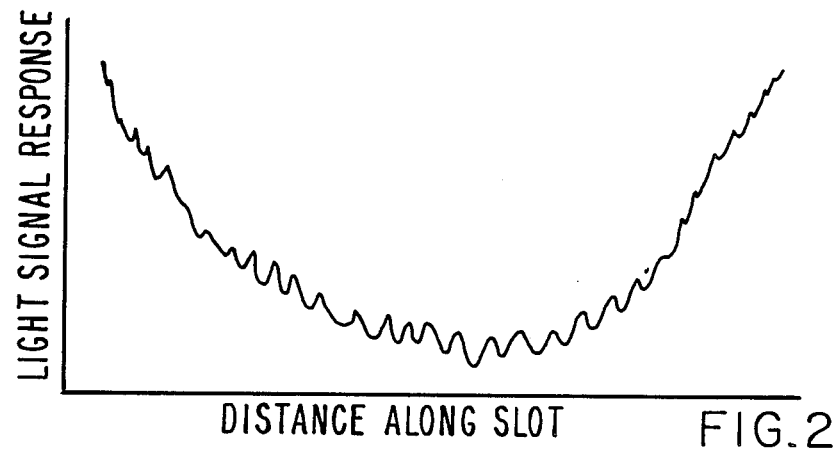
FIG. 2 is a plot of the response signal from photodetectors at the ends of a slotted cylinder of the apparatus versus the distance along the slot for light directed into the cylinder through the slot.
Figure 2A:
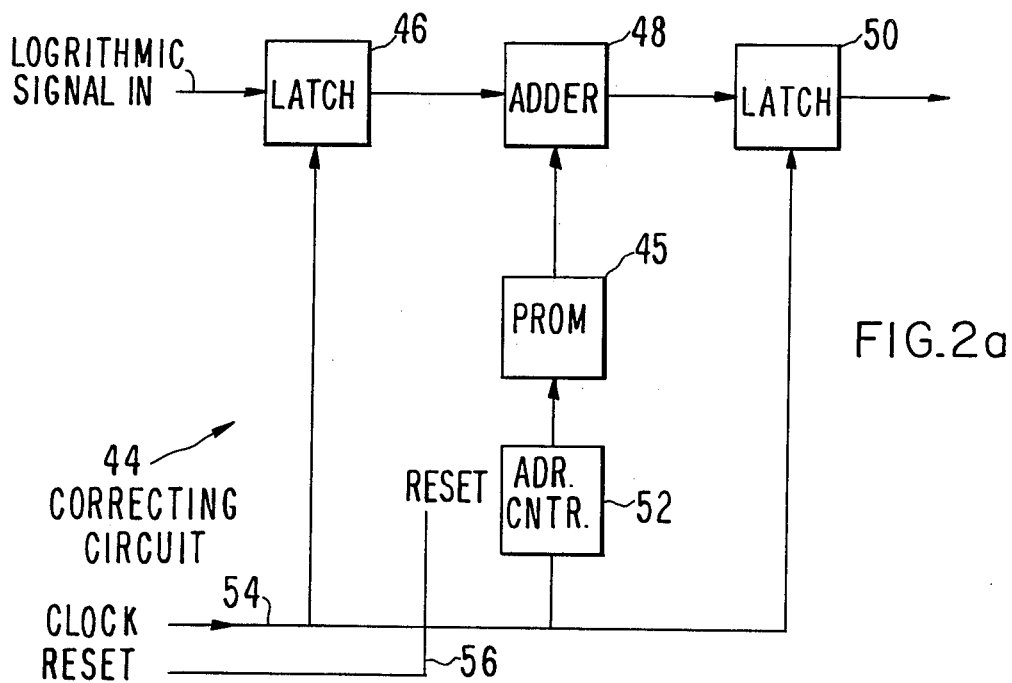
FIG. 2a is a schematic view of a circuit for use in handling the signals generated by the photodiodes when light is received in the cylinder through the slot thereof.

In use, transmitted light with no sheet 20 on frame 12 is first measured at each point along a scan line defined by the slot and stored in a memory 45 of circuit 44 (FIG. 2a). Then, with sheet 20 in place on frame 12, transmitted light is measured along a number of scan lines along the sheet as the frame moves under the influence of motor 16. The scan lines are transverse to the direction of movement of the frame. A typical plot of signal response versus distance along the slot is shown in FIG. 2 for a particular scan line. The data with the sheet in place is corrected by dividing the signal response value for each point along a scan line by the signal response value at the same point with no sheet in place. Equivalently, the logarithm of the data at each point can be calculated and the logarithms for the data with the sheet and with no sheet can then be subtracted by algebraically summing the two values by adder 48.

Figure 3:
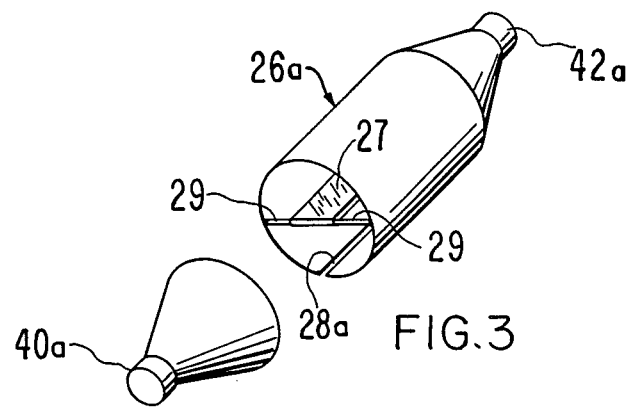
FIG. 3 is a perspective view of a cylinder of a modified form.
Figure 4:
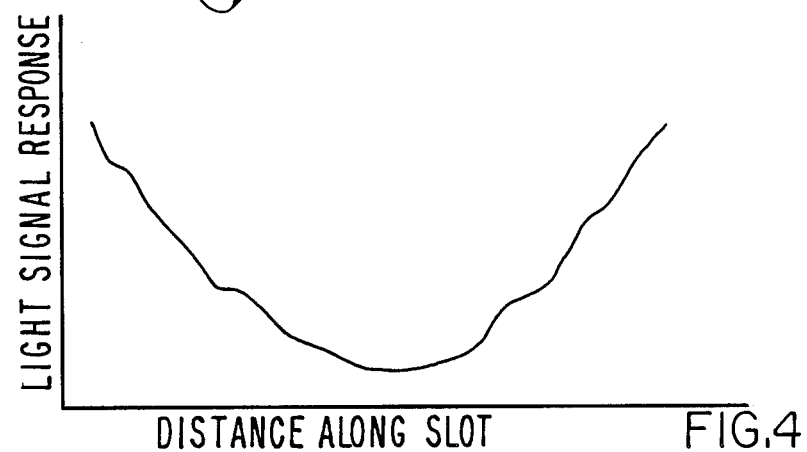
FIG. 4 is a view similar to FIG. 2 but showing the response curve for the cylinder of FIG. 3.

FIG. 3 shows a modified cylinder 26a having a slot 28a and detectors 40a and 42a. The improvement of the cylinder of FIG. 3 is that it includes an elongated, flat diffuser 27 within the cylinder and extending longitudinally of slot 28a. The diffuser is a rigid member which is supported by legs 29 in any suitable manner on the inner surface of the cylinder. Light striking the diffuser is scattered throughout the cylinder and sensed by end photodetectors. The signals for the photodetectors are combined and corrected as described above with respect to cylinder 26. The response curve obtained by using cylinder 26a will be typically as shown in FIG. 4. This smoother curve makes the correction less sensitive to slight errors in the position along the slot.

Figure 5:
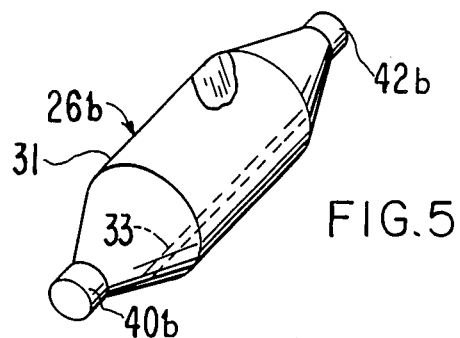
FIG. 5 is a view similar to FIG. 3 but showing another embodiment of the cylinder.

A further embodiment of the cylinder is shown in FIG. 5 and includes a cylinder 26b having a solid, cylindrical glass body 31. The outer surface of the body 31 is coated with a reflective material except along a thin line 33 parallel to the axis of the rod and on the ends of the rod. This thin line 33 is, in effect, a light-receiving slot to allow light to enter the cylinder. A pair of light detectors 40b and 42b are placed with their sensitive surfaces against the ends of the rods. An anti-reflective coating may be used on the ends to maximize the amount of light transferred to the detectors. The signals from the detectors are combined and corrected by circuit 44 for variations in the manner described above with respect to cylinder 26.

Figure 6:
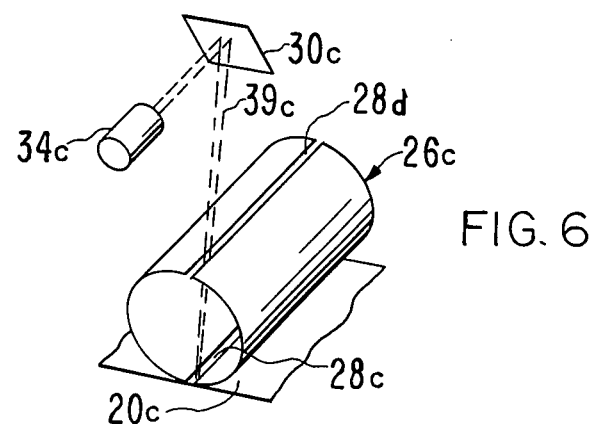
FIG. 6 is a view similar to FIGS. 3 and 5 but showing still another embodiment of the cylinder.

FIG. 6 shows still a further embodiment of the cylinder of the present invention. The cylinder 26c is hollow and includes a first slot 28c and a second slot 28d. Light from source 34c is reflected by a mirror 30c to form a beam 39c which first passes through slot 28d, passes through cylinder 26c and slot 28c and onto sheet 20c. The reflected light from sheet 20c travels in all directions and enters the cylinder through slot 28c. Only a small amount of the scattered light escapes through the entrance slot 28d and most of the light enters the detectors (not shown) at the ends of cylinder 26c and is measured. The correction curve can be generated by measuring the light from a sheet known to be uniformly reflecting. The arrangement shown in FIG. 6 can be used in applications where the image is not on a transparency such as a photographic print.

Radiation from source 34 can be of a number of different wavelengths. The transmittance or reflectance can be measured by detectors 40 (FIG. 1) with filters 41 (in dashed lines) that pass only a narrow band of wavelengths of the radiation and are in front of the detectors.

What is claimed is:

1. Scanning apparatus for taking transmittance or reflectance measurements from a light transmitting or reflecting sheet comprising:
    means for supporting the sheet in an operative position so that the sheet is exposed for being scanned along a line by a radiation beam;
    a radiation source;
    means movable relative to said supporting means for directing a beam of radiation onto the sheet and along a line in scanning relationship thereto when the sheet is in said operative position;
    means defining an elongated cavity having a radiation-receiving slot therein to allow radiation from the line scanning across the sheet to pass into the cavity, the cavity defining means having a radiation-reflecting surface to allow the radiation entering the cavity to be reflected thereby;
    photodetector means for sensing, at the ends of the cavity, the radiation reflected in the cavity and for generating an electronic signal corresponding to the sensed radiation; and
    circuit means coupled with the photodetector means for correcting the signal for variations in the intensity of the radiation entering the cavity as a function of the distance along the slot during scanning of the beam.

2. Apparatus as set forth in claim 1, wherein said cavity defining means includes a cylinder.

3. Apparatus as set forth in claim 2, wherein the cylinder is hollow and has a coating on the inner wall surface thereof, the interior of the cylinder being free of structure.

4. Apparatus as set forth in claim 2, wherein said cylinder is hollow and has a light diffuser therewithin.

5. Apparatus as set forth in claim 4, wherein said light diffuser comprises a flat strip, and means for mounting the strip in the cylinder substantially along the center line thereof.

6. Apparatus as set forth in claim 2, wherein the cylinder is a solid body transparent to the radiation and having a reflecting coating on the outer surface thereof, the body being provided with an elongated groove which is uncoated, said groove defining said slot.

7. Apparatus as set forth in claim 2, wherein the cylinder and the beam directing means being on one side of said operative position of the sheet, said cylinder having a second slot at a location diametrically opposed to the radiation-receiving slot, said radiation-receiving slot being adjacent to said operative position, said beam being directed into the second slot and then into the radiation-receiving slot and onto the sheet for reflectance thereby into the cylinder through the radiation-receiving slot.

8. Apparatus as set forth in claim 1, wherein the radiation from said said radiation source is of a number of different wavelengths, said photodetector means including a filter passing only a narrow band of wavelengths of said radiation.

9. Apparatus as set forth in claim 1, wherein said radiation source includes a plurality of light sources producing a narrow band of radiation centered at different wavelengths of the radiation, said photodetector means being operable to sequentially sense the radiation from said light sources.

10. Apparatus as set forth in claim 1, wherein said photodetector means includes a photodetector at each end, respectively, of the cavity defining means.

11. In scanning apparatus for taking transmittance or reflectance measurements from a radiation transmitting or reflecting sheet mounted in an operative position so that the sheet can be exposed for being scanned along a line by a radiation beam comprising:
    means for directing a beam of radiation onto the sheet and along a line in scanning relationship thereto when the sheet is in said operative position;
    means defining an elongated cavity having a radiation-receiving slot therein to allow radiation from the line scanning across the sheet to pass into the cavity, the cavity defining means having a radiation-reflecting surface to allow the radiation entering the cavity to be reflected;
    photodetector means for sensing at the ends of the cavity the radiation reflected in the cavity and for generating an electronic signal corresponding to the sensed radiation; and
    circuit means coupled with the photodetector means for correcting the signal for variations in the intensity of the radiation entering the cavity as a function of the distance along the slot during scanning of the beam.

12. Apparatus as set forth in claim 11, wherein the cavity defining means is a hollow cylinder having a coating on the inner wall surface thereof, the interior of the cylinder being free of structure.

13. Apparatus as set forth in claim 11, wherein said cavity defining means has a light diffuser therewithin.

14. Apparatus as set forth in claim 13, wherein said light diffuser comprises a flat strip, and means for mounting the strip in the cavity.

15. Apparatus as set forth in claim 11, wherein the cavity defining means is a solid body transparent to the radiation and having a reflecting coating on the outer surface thereof, the body being provided with an elongated groove which is uncoated, said groove defining said slot.

16. Apparatus as set forth in claim 11, wherein the cavity defining means includes a cylinder and the beam directing means adapted to be on one side of said operative position of the sheet, said cylinder having a second slot at a location diametrically opposed to the radiation-receiving slot, said radiation-receiving slot being adjacent to said operative position, said beam being directed into the second slot and then into the radiation-receiving slot and onto the sheet for reflectance thereby into the cylinder through the radiation-receiving slot.

17. Apparatus as set forth in claim 11, wherein the radiation from said said radiation source is of a number of different wavelengths, said photodetector means including a filter passing only a narrow band of wavelengths of said radiation.

18. Apparatus as set forth in claim 11, wherein said radiation source includes a plurality of light sources producing a narrow band of radiation centered at different wavelengths of the radiation, said photodetector means being operable to sequentially sense the radiation from said light sources.

19. Apparatus as set forth in claim 11, wherein said circuit means includes an adder having first and second inputs and an output, conductor means coupling said photodetector means to the first input of the adder, a memory means for storing data corresponding to the values of the signal obtained from scanning along said line when the sheet is out of said operative position, said memory means having an output coupled to said second input, and means for reading out data from said adder.

20. A method of taking radiation measurements from a light transmitting or reflecting sheet comprising:

exposing the sheet for being scanned along a line by a radiation beam;

directing a beam of radiation onto the sheet and along a line in scanning relationship thereto when the sheet is in the operative position;

collecting radiation from the line across the sheet within a cylindrical region and directing the collected light to a predetermined location in said region;

generating an electronic signal corresponding to the collected radiation;

correcting the signal for variations in the radiation entering said cylindrical region as a function of the distance along the slot during scanning of the beam and;

repeating the directing, collecting, generating and correcting steps until at least a part of the area of the sheet has been scanned by the beam.

\* \* \* \* \*